United States Patent [19]

Shiraki et al.

[11] Patent Number: 5,001,228

[45] Date of Patent: Mar. 19, 1991

[54] BIS-ALKYLAMIDE AZO POLYMERIZATION INITIATORS

[75] Inventors: Kazuo Shiraki, Asaka; Tsutomu Miyagawa, Kawagoe, both of Japan

[73] Assignee: Wako Pure Chemical Industries, Ltd., Osaka, Japan

[21] Appl. No.: 385,124

[22] Filed: Jul. 26, 1989

[30] Foreign Application Priority Data

Aug. 1, 1988 [JP] Japan ................ 63-192361

[51] Int. Cl.$^5$ .................. C07C 245/04; C08K 5/23
[52] U.S. Cl. .................... 534/751; 534/640; 534/886; 534/591; 534/190
[58] Field of Search .................. 534/886, 751

[56] References Cited

U.S. PATENT DOCUMENTS 2,877,102  3/1959  Levesque ................ 534/886
3,309,297  3/1967  Takayama et al. ........ 534/886

FOREIGN PATENT DOCUMENTS 68201   8/1944  Norway ................ 534/886
569561  8/1977  U.S.S.R. .............. 54/886

Primary Examiner—Floyd D. Higel
Attorney, Agent, or Firm—Armstrong, Nikaido, Marmelstein, Kubovcik & Murray

[57] ABSTRACT

An azo amide compound of the formula $[N-C(CH_3)_2-CO-NH-R]_2$ or a hydrate thereof or an acid-addition salt thereof, wherein R is $-CH_2CH=CH_2$, benzyl chloride, picolyl, tetrahydropyridylmethyl and N-piperidinoethyl, is useful as a functional polymerization initiator for polymerizing acrylonitrile, methyl acrylate, styrene, vinyl acetate and other vinyl compounds.

7 Claims, No Drawings

BIS-ALKYLAMIDE AZO POLYMERIZATION INITIATORS

BACKGROUND OF THE INVENTION

This invention relates to an azo amide compound useful as a functional polymerization initiator in the production of high polymers.

Recently, the demand for high polymers has changed from general-purpose polymers to functional polymers high in value added. Thus, block polymers and graft polymers which can take a polyphase structure due to a microphase separation structure and are expected to exhibit various functions effectively, have become of interest. Further, by the development of a macromonomer method as a synthesis method for a graft polymer relatively easy in molecular design, it becomes possible to synthesize graft polymers having desired functions. As a result, functional polymerization initiators useful in the synthesis of macromonomers have been and proposed (e.g. Chemical Abstracts 79, 104582p (1973); 86, 122041k (1977); 92, 215869a (1980); Japanese Patent Examined Publication No. 60-18682; Japanese Patent Unexamined Publication No. 61-63643; etc.). In order to meet these demands, further development of functional polymerization initiators has been desired.

SUMMARY OF THE INVENTION

It is an object of the present invention to provide an azo amide compound sufficiently exhibiting properties as a functional polymerization initiator in the synthesis of macromonomers.

The present invention provides an azo amide compound represented by the formula:

$$\left( =N-\underset{\underset{CH_3}{|}}{\overset{\overset{CH_3}{|}}{C}}-\overset{\overset{O}{\|}}{C}-NH-R \right)_2$$

wherein R is a functional group selected from —CH$_2$CH=CH$_2$,

—CH$_2$—⟨C$_6$H$_4$⟩—Cl, —CH$_2$—⟨pyridyl⟩,

—CH$_2$—⟨pyridyl⟩-N, —CH$_2$—⟨cyclohexyl⟩—NH and

—CH$_2$CH$_2$—N⟨piperazinyl⟩NH, or a hydrate thereof, or an acid-addition salt thereof.

BRIEF DESCRIPTION OF THE DRAWING

FIG. 1 of the drawing is the graph showing a relationship between the conversion and the polymerization.

DESCRIPTION OF THE PREFERRED EMBODIMENTS

The azo amide compound of the present invention is represented by the formula:

$$\left( =N-\underset{\underset{CH_3}{|}}{\overset{\overset{CH_3}{|}}{C}}-\overset{\overset{O}{\|}}{C}-NH-R \right)_2 \quad (1)$$

wherein R is a functional group selected from —CH$_2$CH=CH$_2$,

—CH$_2$—⟨C$_6$H$_4$⟩—Cl, —CH$_2$—⟨pyridyl⟩, —CH$_2$—⟨pyridyl-N⟩,

—CH$_2$—⟨cyclohexyl⟩—NH and —CH$_2$CH—N⟨piperazinyl⟩NH, or a hydrate thereof, or an acid-addition salt thereof, and has high activity as a functional polymerization initiator.

As an acid which forms an acid-addition salt with an azo amide compound, there can be used inorganic acids such as hydrochloric acid, sulfuric acid, nitric acid, and the like; organic acids such as acetic acid, propionic acid, lactic acid, benzenesulfonic acid, p-toluenesulfonic acid, methanesulfonic acid, and the like.

Concrete examples of the azo amide compounds of the formula (1), hydrates thereof and acid-addition salts thereof are as follows.

$$\left( =N-\underset{\underset{CH_3}{|}}{\overset{\overset{CH_3}{|}}{C}}-\overset{\overset{O}{\|}}{C}-NH-CH_2CH=CH_2 \right)_2 \quad (2)$$

$$\left( =N-\underset{\underset{CH_3}{|}}{\overset{\overset{CH_3}{|}}{C}}-\overset{\overset{O}{\|}}{C}-NH-CH_2-\text{⟨C}_6\text{H}_4\text{⟩}-Cl \right)_2 \quad (3)$$

$$\left( =N-\underset{\underset{CH_3}{|}}{\overset{\overset{CH_3}{|}}{C}}-\overset{\overset{O}{\|}}{C}-NH-CH_2-\text{⟨pyridyl⟩}\cdot H_2O \right)_2 \quad (4)$$

$$\left( =N-\underset{\underset{CH_3}{|}}{\overset{\overset{CH_3}{|}}{C}}-\overset{\overset{O}{\|}}{C}-NH-CH_2-\text{⟨pyridyl⟩}N\cdot H_2O \right)_2 \quad (5)$$

$$\left( =N-\underset{\underset{CH_3}{|}}{\overset{\overset{CH_3}{|}}{C}}-\overset{\overset{O}{\|}}{C}-NH-CH_2-\text{⟨cyclohexyl⟩}NH\cdot HCl \right)_2 \quad (6)$$

-continued

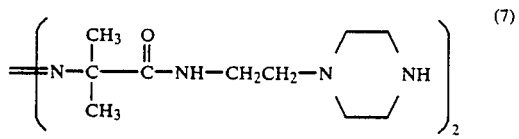

(7)

Properties, solubility and decomposition rate constants of these compounds are listed in Table 1.

TABLE 1

| No. | Formula | Properties | Solubility (15° C.) | | |
|---|---|---|---|---|---|
| (2) | {=N-C(CH₃)₂-C(=O)-NHCH₂CH=CH₂}₂ | White crystals<br>mp. 67° C.~71° C. (dec.)<br>$\lambda_{max}$ 375 nm $\epsilon$33.9(T) | Water | 1% | ↓ |
| | | | Methanol | 10% | ↑ |
| | | | Acetone | 10% | ↑ |
| (3) | {=N-C(CH₃)₂-C(=O)-NHCH₂-C₆H₄-Cl}₂ | White crystalline powder<br>mp. 130° C.~ (dec.)<br>$\lambda_{max}$ 374 nm $\epsilon$31.7(M) | Water | 1% | ↓ |
| | | | Methanol ca. | 5% | |
| | | | Acetone | 10% | ↑ |
| (4) | {=N-C(CH₃)₂-C(=O)-NHCH₂-C₅H₄N·H₂O}₂ | White crystalline powder<br>mp. 104° C.~ (dec.)<br>$\lambda_{max}$ 374 nm $\epsilon$27.1(M) | Water | 1% | ↓ |
| | | | Methanol | 10% | ↑ |
| | | | Acetone | 3% | |
| (5) | {=N-C(CH₃)₂-C(=O)-NHCH₂-C₅H₄N·H₂O}₂ | White crystalline powder<br>mp. 141° C.~ (dec.)<br>$\lambda_{max}$ 374 nm $\epsilon$22.0(M) | Water | 1% | ↓ |
| | | | Methanol ca. | 9% | |
| | | | Acetone | 1% | ↓ |
| (6) | {=N-C(CH₃)₂-C(=O)-NHCH₂-(piperidine-NH)·HCl}₂ | White powder<br>mp. 170° C.~ (dec.)<br>$\lambda_{max}$ 374 nm $\epsilon$29.9(M) | Water | 10% | ↑ |
| | | | Methanol | 10% | ↑ |
| | | | Acetone | 1% | ↓ |
| (7) | {=N-C(CH₃)₂-C(=O)-NHCH₂CH₂-N(piperazine)NH}₂ | White powder<br>mp. 139° C.~ (dec.)<br>$\lambda_{max}$ 374 nm $\epsilon$30.2(H₂O) | Water | 10% | ↑ |
| | | | Methanol | 10% | ↑ |
| | | | Acetone | 1% | ↓ |

| No. | Formula | Solubility (15° C.) | | | Decomposition rate constant |
|---|---|---|---|---|---|
| (2) | {=N-C(CH₃)₂-C(=O)-NHCH₂CH=CH₂}₂ | DMF | 10% | ↑ | 70° C. 7.85 × 10⁻⁷ sec.⁻¹ |
| | | Toluene | 10% | ↑ | 80° C. 2.80 × 10⁻⁶ sec.⁻¹ |
| (3) | {=N-C(CH₃)₂-C(=O)-NHCH₂-C₆H₄-Cl}₂ | DMF | 10% | ↑ | 70° C. 1.34 × 10⁻⁶ sec.⁻¹ |
| | | Toluene ca. | 1% | ↓ | 80° C. 5.44 × 10⁻⁶ sec.⁻¹ |

TABLE 1-continued

| | | | | |
|---|---|---|---|---|
| (4) | ![structure 4: {=N-C(CH3)2-C(=O)-NHCH2-C6H4-N·H2O}2] | DMF<br>Toluene | 1.5%<br>1% ↓ | 70° C. 2.02 × $10^{-6}$ sec.$^{-1}$<br>80° C. 6.88 × $10^{-6}$ sec.$^{-1}$ |
| (5) | ![structure 5: {=N-C(CH3)2-C(=O)-NHCH2-pyridine·H2O}2] | DMF<br>Toluene ca. | 3%<br>1% ↓ | 70° C. 2.36 × $10^{-6}$ sec.$^{-1}$<br>80° C. 8.42 × $10^{-6}$ sec.$^{-1}$ |
| (6) | ![structure 6: {=N-C(CH3)2-C(=O)-NHCH2-piperidine·HCl}2] | DMF<br>Toluene | 1% ↓<br>1% ↓ | 70° C. 4.83 × $10^{-6}$ sec.$^{-1}$<br>80° C. 1.59 × $10^{-6}$ sec.$^{-1}$ |
| (7) | ![structure 7: {=N-C(CH3)2-C(=O)-NHCH2CH2-N(piperazine)NH}2] | DMF<br>Toluene | 1.5%<br>1% ↓ | —<br>— |

As is clear from Table 1, the azo amide compounds of the present invention are solid white crystals or crystalline powders at room temperature. As is clear from the values of decomposition rate constants, the azo amide compounds can be used as a functional polymerization initiators showing high activity at relatively high temperatures. Further, the azo amide compounds except for the compound (6) dissolve in dimethylformamide (DMF) relatively well, and the compounds (2) and (3) have a solubility of as high as 10% or more. To have good solubility in solvents having no hydroxyl group, such as DMF, is remarkably advantageous for carrying out a reaction for introducing a monomer moiety to yield a macromonomer. On the other hand, compound (7) is remarkably high in solubility in water (10% or more) in spite of being a free base form, so that this compound can advantageously be used as a non-salt type water-soluble polymerization initiator.

The above-mentioned compounds have the following functions:

When compound (2) is used as a polymerization initiator, its terminal alkenyl groups are introduced into the polymer and can also polymerization with the monomer(s) and functions as a crosslinking agent. Further, since compound (2) is active at relatively high temperatures, when the polymerization is carried out using together therewith a polymerization initiator having a low temperature activity, compound (2) can be introduced into a polymer without destroying the azo group so as to make it possible to synthesize a pendant type polymer initiator.

When compound (3) is used as a polymerization initiator, it is possible to synthesize a macromonomer by using chlorobenzyl groups at the ends of the polymer obtained by the polymerization.

Further, in case of the compounds (4) and (5), it is possible to synthesize a macromonomer by using pyridyl groups at the ends of the polymer obtained by the polymerization.

Moreover, in case of the compounds (6) and (7), it is possible to synthesize a macromonomer by using amino groups at the ends of the polymer obtained by the polymerization. In addition, it is also possible to form a polymer initiator by reaction with the carboxylic acid moiety in the polymer so as to introduce azo groups into the polymer.

The azo amide compound of the formula (1) can be produced as follows.

An azo ester compound used as a starting material is reacted with an amine in an organic solvent in the presence of a basic catalyst at room temperature, if necessary under cooling (preferably 10°-30° C.) for several hours to several days.

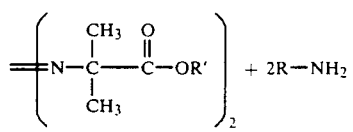

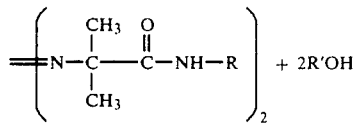

(R'=alkyl, R=as defined above)

As the azo ester compound, there can be used, for example, dimethyl 2,2'-azobis(2-methylpropionate), diethyl 2,2'-azobis(2-methylpropionate), diisopropyl 2,2'-azobis(2-methylpropionate), di-tert-butyl 2,2-azobis(2-methylpropionate), etc.

As the organic solvent, there can be used alcohols such as methanol, ethanol, etc., DMF, dimethylsulfoxide (DMSO), benzene, toluene, carbon tetrachloride, chloroform, dichloroethane, etc.

As the basic catalyst, there can be used a metal alkoxide such as sodium methoxide, sodium ethoxide, potassium tert-butoxide, etc.; sodium hydride or the like which is effective for generating anion which is a conjugated base for the amine used.

The basic catalyst is preferably used in an amount of 1/10 to 1 mole per mole of the amine.

The amine is usually used in an amount of about equivalent weight or slightly in excess.

After the reaction, the desired azo amide compound is separated by a conventional method. For example, the reaction solution is allowed to stand to deposit crystals, or if necessary the reaction solution is concentrated and/or neutralized, and added with water or a suitable is added to deposit crystals, followed by filtration of the deposited crystals. If necessary, the crystals can be purified by, for example, recrystallization.

The starting azo ester compound can be produced, for example, by imino-etherifying 2,2'-azobis-(isobutyronitrile) with an alcohol and hydrogen chloride, followed by hydrolysis, according to a conventional method.

The azo amide compound of the formula (1) can be used as a functional polymerization initiator for polymerizing, for example, acrylonitrile, methacrylonitrile, acrylic acid, methacrylic acid, acrylamide, methacrylamide, methyl acrylate, methyl methacrylate, styrene, vinyl acetate, vinylpyridine, N-vinylpyrrolidine, vinyl chloride, etc.

The present invention is illustrated by way of the following Examples, in which all percents are by weight unless otherwise specified.

EXAMPLE 1

Synthesis of 2,2'-azobis[N-(2-propenyl)-2-methyl propionamide]

Dimethyl 2,2'-azobis(2-methylpropionate) in an amount of 41.9 g, 48 ml of methanol, and 43 g of a 28% $CH_3ONa$ methanol solution were mixed and stirred for dissolution, followed by dropwise addition of 25 g of allylamine to react at 19° to 21° C. for 20 hours.

After the reaction, the reaction solution was concentrated. To the residue, dilute sulfuric acid was added to deposit crystals, followed by filteration of the crystals. After recrystallizing from toluene-hexane, 28.4 g of the desired 2,2'-azobis[N-(2-propenyl)-2-methylpropionamide] was obtained.

$^1$HNMR δppm ($CDCl_3$): 1.36(S, —$CH_3$, 12H), 3.97–4.02 (m, $NHCH_2CH=$, 4H), 5.13–5.22 (m, —$CH=CH_2$, 4H), 5.82–5.96 (m, —$CH=CH_2$, 2H), 6.96 (b, N$\underline{H}$, 2H).

Properties, solubility and decomposition rate constant are as shown in Table 1 in the line of No. (2).

EXAMPLE 2

Synthesis of 2,2'-azobis[N-(p-chlorobenzyl)-2-methylpropionamide]

After mixing 19.3 g of dimethyl 2,2'-azobis(2-methylpropionate), 20 ml of methanol and 20 g of a 28% $CH_3ONa$ methanol solution with stirring for dissolution, 25 g of p-chlorobenzylamine was added thereto dropwise and reacted at 21° to 22° C. for 8 hours.

After the reaction, dilute sulfuric acid was added to the reaction product to deposit crystals. The deposited crystals were filtered and recrystallized from acetone-hexane to yield 23.9 g of the desired 2,2'-azobis-[N-(p-chlorobenzyl)-2-methylpropionamide].

$^1$HNMR δppm ($CDCl_3$): 1.36 (S,—$CH_3$, 12H), 4.49 (d, —$NHCH_2$—, 4H), 7.13 (b, —N$\underline{H}$—,2H), 7.17–7.31 (q. φ, 8H).

Properties, solubility and decomposition rate constant are as shown in Table 1 in the line of No. (3).

EXAMPLE 3

Synthesis of 2,2'-azobis[N-[(pyridine-3-yl)methyl]-2-methylpropionamide]·2$H_2O$.

After mixing 26.6 g of dimethyl 2,2'-azobis(2-methylpropionate), 40 ml of methanol and 40 g of a 28% $CH_3ONa$ methanol solution with stirring for dissolution, 25 g of 3-aminomethylpyridine was poured thereinto and reacted at 18° to 21° C. for 2 days.

After the reaction, the reaction solution was concentrated. To the residue, water was added and deposited crystals were filtered. After washing with acetone, the desired 2,2'-azobis[N-[(pyridin-3-yl)methyl]-2-methylpropionamide]·2$H_2O$ was obtained in an amount of 40.1 g.

$^1$HNMR δppm ($CD_3OD$): 1.50(s, —$CH_3$, 12H),

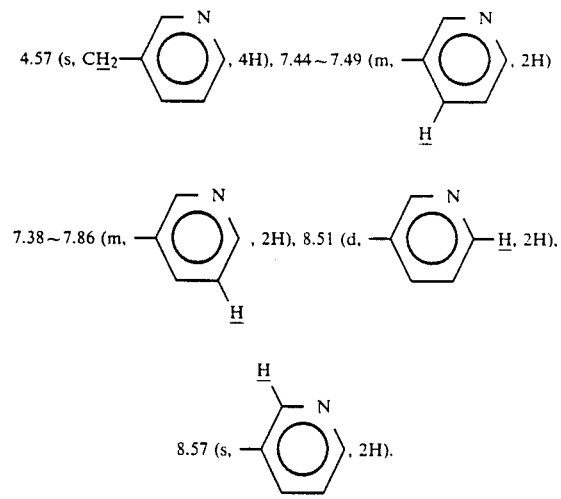

Properties, solubility and decomposition rate constant are as shown in Table 1 in the line of No. (4).

EXAMPLE 4

Synthesis of 2,2'-azobis[N-[(pyridin-4-yl)methyl]-2-methylpropionamide]·2$H_2O$

After mixing 26.6 g of dimethyl 2,2-azobis-(2-methylpropionate), 40 ml of methanol and 40 g of a 28% $CH_3ONa$ methanol solution with stirring for dissolution, 25 g of 4-aminomethylpyridine was poured thereinto and reacted at 18° to 22° C. for 2 days.

After the reaction, deposited crystals were filtered, washed with water and dried to yield 37.2 g of the desired 2,2'-azobis[N-[pyridin-4-yl)methyl]-2-methylpropionamide]·2$H_2O$.

$^1$HNMR δppm ($CD_3OD$): 1.53 (s, —$CH_3$, 12H), 4.60 (s, —$CH_2$—, 4H), 7.42

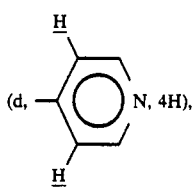

8.54

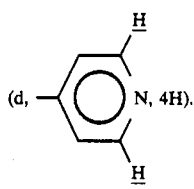

Properties, solubility and decomposition rate constant are as shown in Table 1 in the line of No. (5).

EXAMPLE 5

Synthesis of 2,2'-azobis[N-[(piperidin-4-yl)methyl]2-methylpropionamide]·2HCl

After mixing 25.2 g of 2,2'-azobis(2-methylpropionate), 40 ml of methanol and 20 g of a 28% CH₃ONa methanol solution with stirring for dissolution, 25 g of 4-aminomethylpiperidine was poured thereinto and reacted at 18° to 22° C for 3 days.

After the reaction, 23 ml of a 32% HCl methanol solution was added dropwise to the reaction solution for neutralization. After removing deposited NaCl by filtration, the filtrate was concentrated. The obtained residue was added with acetone to deposit crystals. The deposited crystals were filtered and recrystallized from water-acetone to yield 16.6 g of the desired 2,2'-azobis-[N-[(piperidin-4-yl)methyl]2-methylpropionamide]·2HCl.

¹NMR δppm (CD₃OD): 1.55 (s, —CH₃, 12H), 1.5-1.7, 2.0-2.2

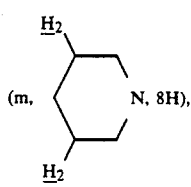

3.1-3.25,

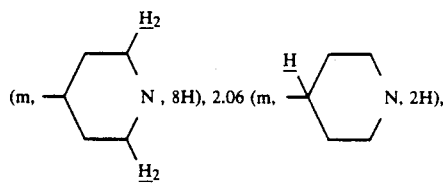

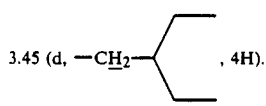

Properties, solubility and decomposition rate constant are as shown in Table 1 in the line of No. (6).

EXAMPLE 6

Synthesis of 2,2'—azobis[N-[piperazine-1-yl)ethyl]-2-methylpropionamide]

After mixing 22.3 g of dimethyl 2,2'-azobis(2-methylpropionate), 20 ml of methanol and 20 g of a 28% CH₃ONa methanol solution with stirring for dissolution, 25.0 g of N-aminoethylpiperadine was poured thereinto and reacted at 18° to 21° C. for 3 days.

After the reaction, deposited crystals were filtered and recrystallized from benzene-hexane to yield 16.8 g of the desired 2,2'-azobis[N-[(piperdin-1-yl)-ethyl]-2-methylpropionamide].

¹HNMR δppm (CD₃OD): 1.53 (s, —CH₃, 12H),

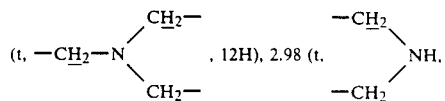

8H), 3.33 (t, —CONHC$\underline{H}_2$—, 4H).

Properties, solubility and decomposition rate constant are as shown in Table 1 in the line of No. (7).

EXAMPLE 7

Using the azo amide compounds (2) to (7) as polymerization initiators, a solution polymerization of acrylonitrile was carried out under the following polymerization conditions and polymerization method.

Polymerization conditions

| | |
|---|---|
| Charged amount of acrylonitrile: | 2.5 ml |
| Polymerization initiator concentration: | 1.42 × 10⁻² mole/l |
| Solvent: | dimethylsulfoxide (DMSO) 10 ml |
| Polymerization temperature: | 80° C. |

Polymerization method

In a polymerization tube made of pyrex, 10 ml of DMSO dissolving a polynmerization initiator in the predetermined amount and 2.5 ml of the monomer were placed. After replacing the air by N₂, dissolved oxygen was removed and the tube was sealed. The tube was heated to 80° C. to carry out the polymerization for a predetermined time. Then, the tube was opened and the reaction solution was poured into 150 ml of methanol to deposit and precipitate the obtained polymer. The precipitate was filtered with a glass filter, washed with 200 ml of methanol, and dried under reduced pressure. The weight of the polymer obtained was measured and the conversion was calculated from the following equation:

$$\text{Conversion } (\%) = \frac{\text{Weight of dried polymer}}{\text{Weight of monomer charged}} \times 100$$

Results

The relationship between the polymerization time and the conversion is shown in the attached drawing, wherein the azo amide compounds used are shown by the following curves:

| | | | | | |
|---|---|---|---|---|---|
| Compound (2) | — | △ | — | △ | — |
| Compound (3) | — | ◇ | — | ◇ | — |
| Compound (4) | — | ○ | — | ○ | — |
| Compound (5) | — | ▲ | — | ▲ | — |
| Compound (6) | — | ◆ | — | ◆ | — |
| Compound (7) | — | ● | — | ● | — |

As mentioned above, the azo amide compounds of the formula (1) are useful as azo series radical polymerization initiators showing high activity at relatively high temperatures. Further, the azo amide compounds of formula (1) are excellent in solubility in various solvents. Moreover, since the azo amide compounds of the formula (1) have characteristic functional groups rich in reactivity, use as a functional polymerization initiator for, e.g. synthesis of macromonomers, can be expected.

What is claimed is:

1. An azo amide compound represented by the formula:

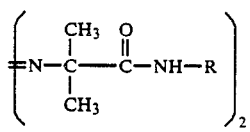

wherein R is a functional group selected from —CH₂CH=CH₂,

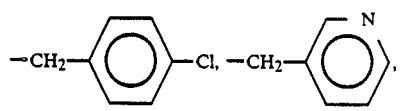

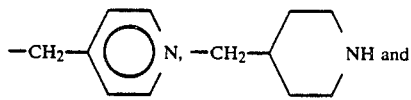

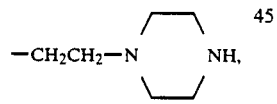

or a hydrate thereof, or an acid-addition salt thereof.

2. A compound according to claim 1, which is

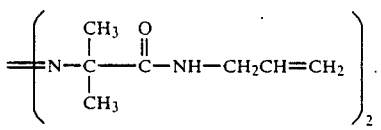

3. A compound according to claim 1, which is

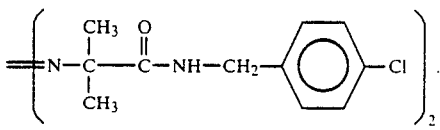

4. A compound according to claim 1, which is

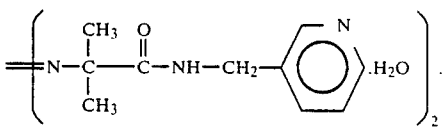

5. A compound according to claim 1, which is

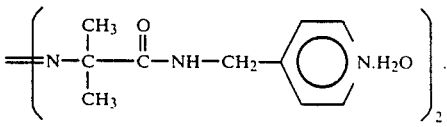

6. A compound according to claim 1, which is

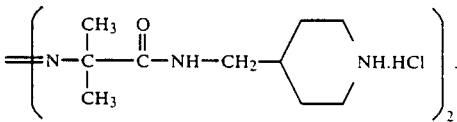

7. A compound according to claim 1, which is

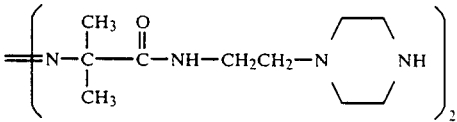

* * * * *